(12) United States Patent
Rucker

(10) Patent No.: US 10,994,087 B2
(45) Date of Patent: May 4, 2021

(54) VAPOUR PRODUCING DEVICE WITH A REMOVABLE CONTAINER AND A REMOVABLE CONTAINER FOR USE WITH SUCH A DEVICE

(71) Applicant: Simon Rucker, London (GB)

(72) Inventor: Simon Rucker, London (GB)

(73) Assignee: Simon Rucker, London (GB)

( * ) Notice: Subject to any disclaimer, the term of this patent is extended or adjusted under 35 U.S.C. 154(b) by 255 days.

(21) Appl. No.: 16/331,943

(22) PCT Filed: Sep. 8, 2017

(86) PCT No.: PCT/GB2017/052637
§ 371 (c)(1),
(2) Date: Mar. 8, 2019

(87) PCT Pub. No.: WO2018/046946
PCT Pub. Date: Mar. 15, 2018

(65) Prior Publication Data
US 2019/0239567 A1    Aug. 8, 2019

(30) Foreign Application Priority Data

Sep. 9, 2016 (GB) .................... 1615359

(51) Int. Cl.
*A24F 47/00* (2020.01)
*A61M 15/06* (2006.01)
*A61M 11/04* (2006.01)
*A24F 40/42* (2020.01)
*A24F 40/46* (2020.01)
*A61M 15/08* (2006.01)
*A24F 40/20* (2020.01)

(52) U.S. Cl.
CPC ............. *A61M 15/06* (2013.01); *A24F 40/42* (2020.01); *A24F 40/46* (2020.01); *A61M 11/042* (2014.02); *A24F 40/20* (2020.01); *A61M 15/08* (2013.01); *A61M 2205/3653* (2013.01); *A61M 2205/8206* (2013.01)

(58) Field of Classification Search
CPC ........................... A24F 47/008; A61M 11/042
USPC ....................................................... 131/329
See application file for complete search history.

(56) References Cited

U.S. PATENT DOCUMENTS

| | | | |
|---|---|---|---|
| 5,388,594 A | 2/1995 | Counts et al. | |
| 10,028,533 B2 * | 7/2018 | Fursa | H03F 3/2176 |
| 10,219,543 B2 * | 3/2019 | Gill | B65D 43/02 |
| 10,834,972 B2 * | 11/2020 | Mironov | A24F 47/008 |
| 2007/0102013 A1 | 5/2007 | Adams et al. | |
| 2010/0101590 A1 | 4/2010 | Pflum | |
| 2012/0234315 A1 * | 9/2012 | Li | A24F 40/465 |
| | | | 128/200.21 |

(Continued)

FOREIGN PATENT DOCUMENTS

| | | |
|---|---|---|
| GB | 2527597 | 12/2015 |
| WO | WO 2015/116934 | 8/2015 |
| WO | WO 2015/172224 | 11/2015 |

*Primary Examiner* — Neil Abrams
(74) *Attorney, Agent, or Firm* — Levy & Grandinetti

(57) ABSTRACT

A vapour producing device has a power supply, a heater powered by the power supply, a heating chamber heated by the heater, and a vapour outlet, in which a removable container is disposed in the heating chamber. The removable container has a vapour permeable membrane enclosing a herbal vapour producing material to be heated.

6 Claims, 6 Drawing Sheets

(56) References Cited

U.S. PATENT DOCUMENTS

2012/0247494 A1   10/2012  Oglesby et al.
2016/0295921 A1*  10/2016  Mironov ................ H05B 6/105
2019/0239567 A1*   8/2019  Rucker .................. A24F 40/46

* cited by examiner

VAPOUR PRODUCING DEVICE WITH A REMOVABLE CONTAINER AND A REMOVABLE CONTAINER FOR USE WITH SUCH A DEVICE

The present invention relates to a vapour producing device with a removable container, and a removable container for use with such a device, for use particularly, but not exclusively, to vaporise herbal materials.

Herbal vaporisers are electronic devices which heat a herbal material to a pre-determined temperature in a heating chamber in order to release an aerosol for consumption. The herbal material is not burnt, rather it is heated only sufficiently for the active ingredient to boil and be released as a consumable vapour. Such devices are distinct from electronic atomisers or e-cigarettes which heat a prepared liquid product to release an aerosol for consumption.

Herbal vaporisers are a less harmful way to consume a herbal product like tobacco or medical marijuana than smoking it, because the aerosol contains far less of the many carcinogenic, mutagenic and teratogenic bi-products created by combustion.

In comparison to atomisers and the like which can produce a consumable vapour at any time, herbal vaporisers are beneficial because they heat all the herbal material placed in them at once, meaning that users have to make a conscious decision to use them. This means users can more easily regulate or track their consumption, which may increase their chance of quitting.

However, known herbal vaporisers are designed to heat loose herbal material, which has to be ground to the correct particle size, and then has to be loaded manually into a heating chamber of the device before the consumption process is begun. The waste material then has to be removed therefrom at the end. This approach appeals to some, who may enjoy the process. However, for others it is time consuming, and can be messy and fiddly. In particular, it may be considered a disadvantage in comparison to atomizers and the like, which consume easy to load cartridges of liquid. These are much easier to use on the go than herbal vaporisers. As such, some people may not adopt herbal vaporisers for these reasons.

In addition, when loose herbal material is placed into the heating chamber of a device, it may be arranged irregularly therein, in particular if the heating chamber is not fully filled with material. As such, the process of heating the loose material may not be optimal, as the conduction of heat from the inner surface of the heating chamber may not reach it all, or may not heat it all in a regular manner.

The present invention is intended to overcome some of the above described problems. Therefore, according to a first aspect of the present invention a vapour producing device comprises a power supply, a heater powered by said power supply, a heating chamber heated by said heater and a vapour outlet, in which a removable container is disposed in said heating chamber, said removable container comprising a vapour permeable membrane enclosing a herbal vapour producing material to be heated.

Thus, the present invention overcomes the above described problems by providing a container for the herbal product to be consumed. The removable container can be produced as a consumable product, with prepared herbal material inside it, which can then be placed in the vapour producing device for consumption in a simplex action, and then removed therefrom after the herbal product has been heated, again in a simplex action. This removes from the end user the requirements to prepare the loose herbal material, to load the device manually with it, and then to empty and clean it at the end of the process.

The removable container of the invention can be constructed in any known way, either fully or partly of any known vapour permeable material. All that is required for the invention to be performed is that the herbal material is contained therein for consumption, and that the vapour produced in use can be released.

In one version of the invention the heating chamber can comprise a receptacle area with an inner surface of a pre-determined three-dimensional shape, and the removable container can be formed with a shape which substantially corresponds with this pre-determined three-dimensional shape. Therefore, the maximum contact area is created between the inner surface of the receptacle area and the removable container, which may improve the efficiency of the heating process, because the conduction of heat from the inner surface of the heating chamber is applied to the removable container equally around its surface, and therefore transmitted to the herbal vapour producing material inside in a more efficient manner than in known examples.

In addition, the use of a removable container which is the same size and shape as the receptacle area of the heating chamber ensures that the heating chamber is fully filled with herbal material, and that the amount consumed is the same every time. This allows users to readily regulate and track their consumption.

The receptacle area can be any shape, but in one version of the invention it can be substantially rectangular. This may be the most viable shape as many known herbal vaporisers have a generally rectangular cross-sectional axial shape. If so, the inner surface of the receptacle area can comprise rounded edges. This feature makes the receptacle area, and the removable container, a more ergonomic and attractive shape. It also improves the heating efficiency, as the conduction of heat via a rounded corner is more efficient than at a right-angled corner where contact between surfaces is more readily lost.

In addition, and as referred to in more detail below, the method of manufacture of the removable container is an important consideration, and a rectangular removable container can be produced using known manufacturing methods from other technical fields. Adopting such a method, and using known machinery, could significantly reduce the innovative burden required to bring the present invention to fruition.

In an alternative embodiment of the invention the receptacle area can be substantially annular. This may be preferred for similar reasons to as above. Namely, some known herbal vaporisers comprise an annular receptacle area, which could receive an annular removable container. An annular configuration would also generate an efficient heating arrangement. Furthermore, there are other known manufacturing methods which could be adopted here, and which would produce a substantially round or cylindrical removable container.

The vapour producing device can comprise a mouthpiece, which can comprise the vapour outlet, and which can be removably mountable over the heating chamber to enclose the removable container therein. Some known herbal vaporisers have this kind of structure, as it is an efficient axial arrangement of components. The heating chamber can be readily accessed under the mouthpiece, and the vapour produced in use is channeled directly to the vapour outlet above. With a device of the present invention the loading and unloading of the removable container would simply involve removing the mouthpiece and placing or removing the removable container from the exposed heating chamber.

Alternatively, the vapour producing device can comprise a cover which can be removably mountable over the heating chamber to enclose the removable container therein. Some other known herbal vaporisers have this kind of structure, with the heating chamber on the side of the device. This may be preferred for aesthetic reasons, or if no removable mouthpiece is used.

Preferably the vapour producing device can comprise a mounting platform adjacent to the receptacle area, and the removable container can comprise a mounting flange which can be shaped and configured so as to be mounted on the mounting platform. This arrangement facilitates the ready interface between the device and the removable container, because co-operation between the mounting platform and the mounting flange can serve to locate the removable container in the heating chamber correctly. The mounting flange also provides a means to manually manipulate the removable container, in order to place it inside the heating chamber, and to remove it therefrom. It can also serve to maintain a part of the removable container in a particular position, for example the top in the plane of the mounting platform. This is advantageous if the removable container has a flexible shape which may otherwise collapse into the heating chamber.

In some embodiments of the invention the removable container can comprise a laterally extending handle portion, and the device can comprise a seating area in which the handle portion can be located. This feature adds an additional level of usability, because the user can readily manually manipulate the removable container. The removable container may be fairly small, so the handle portion may be particularly useful.

In one version of the invention the removable container can comprise a body portion, an opening formed in the body portion, and a lid portion closing the opening. The body portion can comprise a first connection region, the lid portion can comprise a second connection region, and the first connection region and the second connection region can be connected together by a connection means comprising one or more of a heat seal component, an adhesive component, an ultrasonic weld, a crimping component, a stitching component, a staple component or a punched material component. A construction of this kind can be produced using known manufacturing methods. In particular, there are various ways to affix materials together using known additives, such as heat seals, adhesives, ultrasonic welds and so on, and any could be used here. Further, it is also known to affix materials together directly, using structures like crimps, punches or burst hole joints and the like, which use the folded or manipulated material of one part as a means to connect it to the other. The body portion can be filled with herbal product before the lid portion is then applied and fixed in place.

Of course, there will be operational requirements which must be met. In particular, the connection means of the invention will have to be able to withstand the heating provided by the heating chamber in use without permanently failing. The heating chambers of herbal vaporisers typically reach up to about 200 degrees centigrade. Some known connection means may fail at this temperature, but others not.

In terms of heat seal components there are several known options which could be used in the present invention. A first option is to use heat sealable filter papers made from rayon which are impregnated with thermoplastic fibres as the material of the removable container. These are suitable because they are vapour permeable and the thermoplastic fibres would constitute a heat seal component.

A first type uses polypropylene. However, this is not biodegradable, and it melts at 165 degrees centigrade. As such, it may fail at some point in use. However, it would reseal as the temperature decreases after use. A second type uses polyethylene, but this is also not biodegradable and it melts at up to 130 degrees centigrade, so this may also fail. Further, it is not known what kind of emissions would be released from the thermal decomposition of polypropylene or polyethylene. A third type uses polylactide. This is at least biodegradable, but its melting point is about 150 degrees, so this may also fail at some point in use.

A second option is to use non heat seal grades of filter paper as the material for the removable container. These are commonly used to manufacture tea bags, and are sometimes held together with crimps or staples. Such connection means would be able to withstand the temperatures experienced inside a herbal vaporiser without failing.

Another option is non heat seal papers which contain polyester fibres. These are used to increase strength, and are common to single serve coffee capsules. The material is usually ultrasonically welded to a structural capsule part. Polyester melts at 265 degrees centigrade so it would withstand the temperature inside the heating chamber.

Known types of adhesives which are capable of withstanding 200 degrees centigrade could also be used. As could any kind of stitching, staples or crimping components. Manufacturing methods which utilise such connection mechanisms are all known, and could be used here, either in isolation or in combination.

In a preferred construction the opening of the body portion of the removable container can be planar, the body portion can comprise a rim which defines the opening, and the first connection region can comprise a flange extending substantially parallel with the opening. The lid portion can then be planar and the second connection region can comprise a peripherally extending region of the lid portion. With this construction the flange and the second connection region can combine to form the mounting flange as described above. This construction is also beneficial because the flange and the peripherally extending region of the lid portion are overlaid, providing a strong connection arrangement.

In an alternative construction the removable container can comprise a first part partially connected to a second part so as to form a container comprising an opening. The removable container can then comprise a connection means closing the opening comprising one or more of a heat seal component, an adhesive component, an ultrasonic weld, a crimping component, a stitching component, a staple component or a punched material component. This construction can also be made using known manufacturing techniques. In particular, two parts connected in this way is a very simple construction which may require very few manufacturing steps. The resulting removable container would have the characteristics of a tea bag or the like. The herbal product can be placed inside the removable container through the opening before it is then closed. Alternatively, if the manufacturing process allows for it, the first part and the second part of the removable container could be wrapped around the herbal product before they are then connected together in a single step using any of the connection means described above, without any opening as such being formed.

In yet another alternative embodiment the removable container can be formed from a tube of material which is closed at both ends by one or more of a heat seal component, an adhesive component, an ultrasonic weld, a crimping component, a stitching component, a staple component or a punched material component. Yet again, such a construction is possible with known manufacturing techniques. In particular, methods of making continuous tubes of material from flat strips which are either folded and crimped, or heat sealed along the long edges may be used here. Also, continuous tubes of material can also be made via extrusion or helical winding techniques. Such tubes can be cut to size, filled with herbal material and then closed at both ends to make another kind of tea-bag like removable container.

It will be appreciated that the vapour permeable membrane can be all of the material of the removable container, or just a part of it. However, preferably the majority of the removable container is the vapour permeable membrane to best release the herbal vapour for the user. It will also be appreciated that any known material which is capable of releasing vapour could be used, several of which are described above, however there are various operational factors which can be improved if the right kind of material is used. For example, the material should release as much of the vapour produced as possible to maximise the experience, but it must also be able to withstand the temperature of the heating chamber in use without combusting or otherwise releasing undesirable potentially toxic emissions. Further, it must also retain the herbal material during manufacture, packaging, storage, transport and user handling. It must have sufficient strength to withstand the forces it will be subjected to in normal usage without breaking. The skilled person will be able to choose the material, its density, and other characteristics to arrive at a functioning solution.

The vapour permeable membrane can comprise any one of a paper material, a plastics material, a plastics reinforced paper material or a woven material or a perforated metal material.

As discussed above, the removable container could be constructed from known types of heat sealable filter paper, or non heat sealable filter paper. These are all vapour permeable so can from the vapour permeable membrane of the invention. The removable container could also comprise a woven material like muslin, which could be stitched together to form the removable container. Woven materials are also vapour permeable.

In one version of the invention the vapour permeable membrane perishes when the removable container is heated by the heater in use. Such an arrangement is beneficial because the removable container does not need to be removed from the heating chamber after it has been used. It might also allow for cheaper or more readily available materials to be used for the removable container. However, it would have the disadvantage that the material of the removable container would mix with the vapour produced in use, which could be a big disadvantage.

It will be appreciated that the invention relates to two kinds of products, the vapour producing device itself, but also the consumable removable containers. It is possible that manufacturers would produce both, but also that they would only produce the removable containers.

Therefore, according to a second aspect of the present invention a removable container for use in creating a vapour producing device as claimed in any of claims 1 to 15 below, in which the removable container comprises a vapour permeable membrane enclosing a herbal vapour producing material to be heated.

As outlined above, the container can be substantially rectangular, substantially annular, it can comprise a mounting flange, and/or it can comprise a laterally extending handle portion.

It can also comprise a body portion, an opening formed in the body portion, and a lid portion closing the opening. The body portion can comprise a first connection region, the lid portion can comprise a second connection region, and the first connection region and the second connection region can be connected together by a connection means comprising one or more of a heat seal component, an adhesive component, an ultrasonic weld, a crimping component, a stitching component, a staple component or a punched material component. The opening can be planar, the body portion can comprise a rim which defines the opening, the first connection region can comprise a first flange extending substantially parallel with the opening, the lid portion can be planar, and the second connection region can comprise a peripherally extending region.

Alternatively the removable container can comprise a first part partially connected to a second part so as to form a container comprising an opening, and the removable container can comprise a connection means closing the opening comprising one or more of a heat seal component, an adhesive component, an ultrasonic weld, a crimping component, a stitching component, a staple component or a punched material component.

Alternatively, the removable container can be formed from a tube of material which is closed at both ends by one or more of a heat seal component, an adhesive component, an ultrasonic weld, a crimping component, a stitching component, a staple component or a punched material component.

The vapour permeable membrane can comprise any one of a paper material, a plastics material, a plastics reinforced paper material, a woven material or a perforated metal material.

The first and second aspects of the present invention can be performed in various ways, but nine embodiments will now be described by way of example and with reference to the accompanying drawings, in which FIG. 1 is a cross-sectional side view of a vapour producing device according to the first aspect of the present invention;

Figure 1:
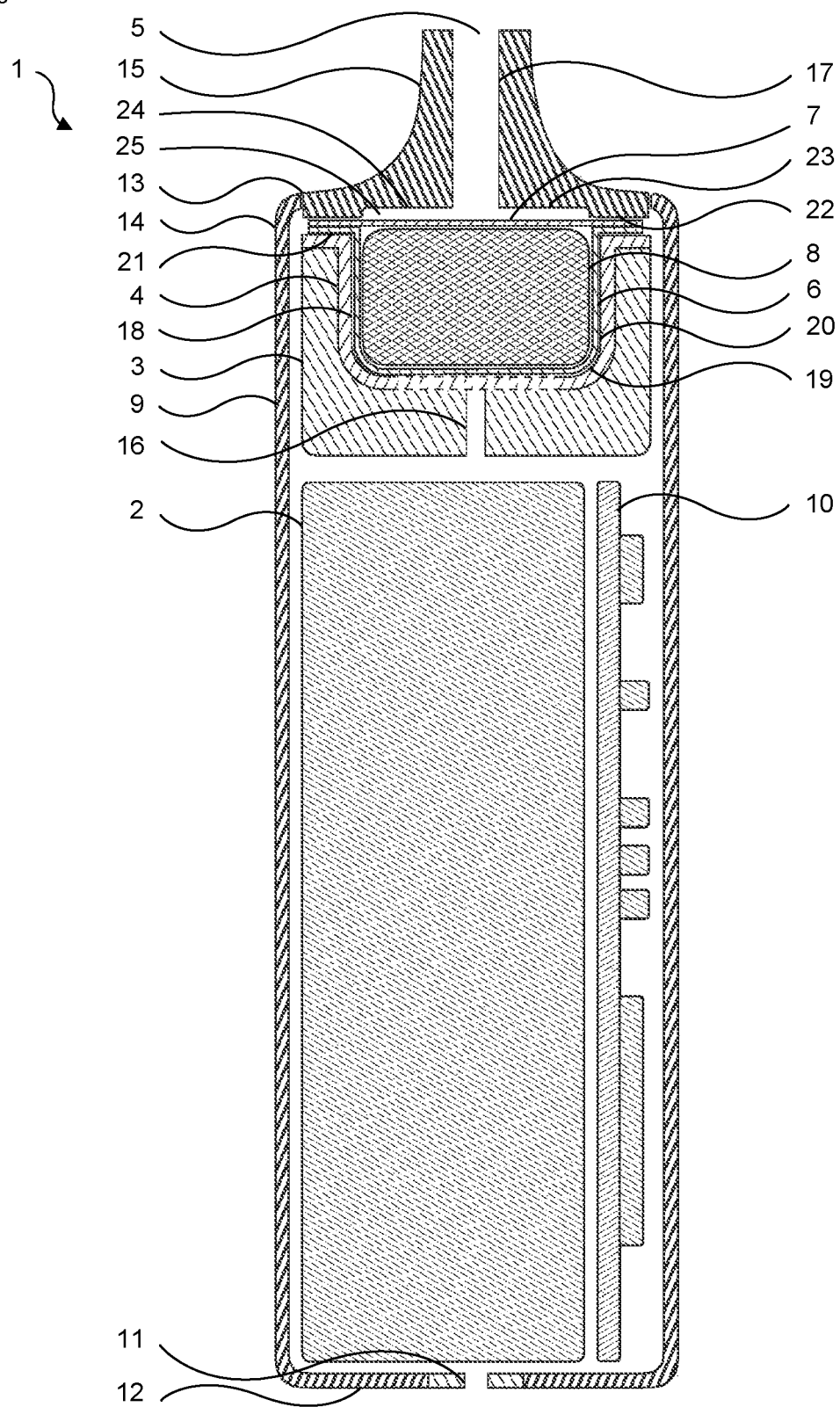

As shown in FIG. 1 a vapour producing device 1 comprises a power supply, in the form of rechargeable battery 2, a heater 3 powered by the power supply (2), a heating chamber 4 heated by the heater 3 and a vapour outlet 5, in which a removable container 6 is disposed in the heating chamber 4, the removable container 6 comprising a vapour permeable membrane 7 enclosing a herbal vapour producing material 8 to be heated.

The device 1 is similar to known herbal vaporisers, and it comprises an outer body 9, which is elongate and has a rectangular cross-sectional shape. The battery 2 is housed inside the body 9, alongside a controlling PCB 10. The PCB 10 operates in the known way, and supplies power to the heater 3 when the device 1 is activated in use. A power socket 11 is provided at a bottom 12 of the device 9 for recharging the battery 2.

Arranged on top of the battery 2 and PCB 10 is the heater 3 and the heating chamber 4. Disposed inside the heating chamber 4 is the removable container 6. The body 9 has an opening 13 at a top 14 thereof, which provides unrestricted access to the heating chamber 4. The opening 13 is closed by a mouthpiece 15, which is a resilient snap-fit in the opening 13.

An air passageway 16 is provided through the heater 3, and a vapour passageway 17 is provided in the mouthpiece 15. As such, the user can draw vapour produced in use by sucking on the mouthpiece, because the air passageway 16 prevents any back pressure from building up.

As is clear from FIG. 1, the heating chamber 4 comprises a rectangular receptacle area 18 with rounded edges 19 and an inner surface 20.

A mounting platform 21 is provided adjacent to the receptacle area 18. It extends around the whole periphery of the receptacle area 18, and is therefore rectangular in shape.

The mouthpiece 15 comprises a retention surface 22 on its underside 23, which is arranged above the mounting platform 21 when the mouthpiece 15 is fitted in the opening 13, and is a corresponding rectangular shape to the mounting platform 21.

The underside 23 of the mouthpiece 15 also features a recess 24, such that when it is fitted in the opening 13 an air gap 25 is provided above the removable container 6. This allows vapour to be drawn upwards from the area of the herbal material 8 and into the vapour passageway 17 in use.

Figure 2:
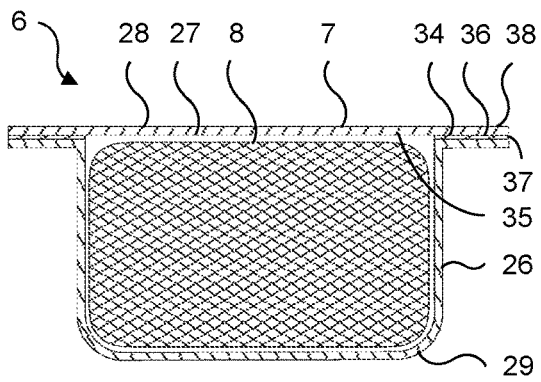
FIG. 2 is a cross-sectional side view of a first removable container according to the second aspect of the present invention for use with the vapour producing device as shown in FIG. 1.
Figure 3:
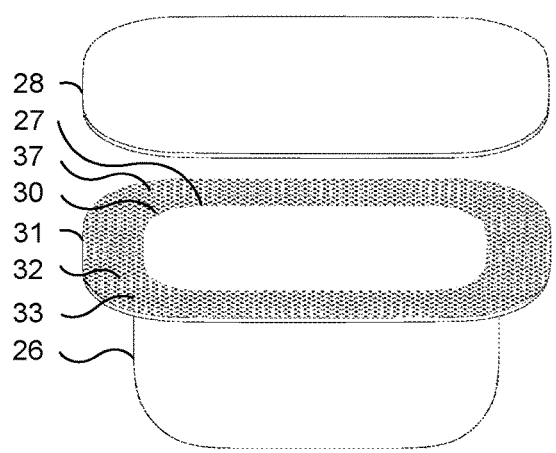
FIG. 3 is an exploded perspective view of the first removable container shown in FIG. 2.

Referring to FIGS. 2 and 3, the removable container 6 comprises a body portion 26, an opening 27 formed in the body portion 26, and a lid portion 28 closing the opening 27. The removable container 6 has a shape which corresponds to that of the receptacle area 18, so it is rectangular with rounded edges 29. As such, the maximum contact area is created between the inner surface 20 and the removable container 6 when it is disposed in the heating chamber 4, which ensures the most efficient heating process. Furthermore, the rounded edges 19 and 29 also improve the heating efficiency, as the conduction of heat via a rounded corner is more efficient than at a right-angled corner where contact between surfaces is more readily lost.

As is clear from FIGS. 2 and 3 the opening 27 is planar, and the body portion 26 comprises a rim 30 which defines the opening 27. A flange 31 extends substantially parallel with the opening 27, around the whole of the rim 30. The lid portion 28 is also planar, and corresponds in perimeter to the flange 31.

An upper side 32 of the flange 31 comprises a first connection region 33, and a peripherally extending region 34 of the underside 35 of the lid portion 28 which corresponds in shape to the flange 31 comprises a second connection region 36. A connection means in the form of a heat seal 37 is provided between the first connection region 33 and the second connection region 36 to bond them together.

The body portion 26 and the lid portion 28 are made from a heat sealable filter paper material, and the heat seal 37 is formed from plastics fibres contained in the filter paper material, which are heated to their melting point during manufacture so as to form a bond. This is a known sealing technique, and would be done once the body portion 26 was filed with the required quantity of herbal material 8.

The bond formed between the first connection region 33 and the second connection region 36 may not withstand the temperatures generated by the heater 3 in use, and the bond may fail. However, as the temperature inside the device 1 decreases after use the bond is reformed.

As explained above this is just one of a number of different materials and connection means which can be used with the present invention, and a number of other types are used in the further embodiments described below.

The flange 31 and the second connection region 36 combine to form a mounting flange 38 which is shaped and configured so as to mount on the mounting platform 21, as shown in FIG. 1, when the body portion 26 of the removable container 6 is disposed in the heating chamber 4. It is also held in that position by the retention surface 22 of the mouthpiece 15. It will be appreciated that this configuration ensures the correct placement of the removable container 6 in the device 1, and it also ensures that the lid portion 28 is held in the plane of the mounting platform 21, which is advantageous because the body portion 26 and the lid portion 28 are flexible, and the removable container would otherwise collapse to a certain extent into the heating chamber 4. It also ensures that if the bond between the first connection region 33 and the second connection region 36 fails in use these two parts are still held firmly together, so that the bond may re-form when the device 1 cools back down again.

It will be appreciated that as the mounting flange 38, and therefore the heat seal 37, sits outside of the heating chamber 4, it will not be heated thereby to the same temperature as the body portion 26. This arrangement means that the bond between the first connection region 33 and the second connection region 36 may not fail in use.

Furthermore, the mounting flange 38 also provides a means for the user to manually manipulate the removable container 6, in order to place it inside the heating chamber 4, and to remove it therefrom.

As explained above both the body portion 26 and the lid portion 28 are constructed from a plastics reinforced filter paper material. This material is vapour permeable, and as such both the body portion 26 and the lid portion 28 comprise the vapour permeable membrane 7 of the present invention. It will be appreciated that the majority of the vapour produced in use will permeate through the lid portion 28 as it faces the air gap 25 and the vapour passageway 17. However some will also permeate through other parts of the body portion 26.

This filter paper material and its density is also chosen because it is capable of withstanding the temperature of the heating chamber 4 in use without combusting or otherwise releasing undesirable by-products. Further, it is also has sufficient strength to retain the herbal material 8 during manufacture, packaging, storage, transport and user handling of the removable container 6.

In use the device 1 operates as follows. The battery 2 is first charged via the charging socket 11, until at least sufficient power to operate the heater 3 is stored. The user then removes the mouthpiece 15 from the opening 13 to expose the receptacle area 18. The removable container 6 is then placed into the heating chamber 4, with the body portion 26 disposed in the receptacle area 18 and the mounting flange 38 on the mounting platform 21. The mouthpiece 15 is then fitted into the opening 13, with the retention surface 22 applied to the mounting flange 38 to secure the removable container 6 in place.

The device 1 is then operated in the known way to drive the heater 3. An operation trigger (not shown) is pressed, and the PCB provides a power supply from the battery 2 to the heater 3. The heater 3 heats up until the inner surface 20 has reached a pre-determined temperature in the region of 200 degrees centigrade. At this point the herbal material 8 releases the consumable vapour. The device 1 comprises an indication light (not shown) which illuminates to indicate to the user that this temperature has been reached and the device 1 is ready to be used.

The user then places the vapour outlet 5 in their mouth and draws on it. The vapour produced by the herbal material 8 passes through the permeable membrane 7, into the airgap 25 and up the vapour passageway 17 to the vapour outlet 5. The air passageway 16 allows for the vapour to flow freely in this way without any back pressure building up.

The heater 3 continues to heat the removable container 6 for a pre-determined period of time which corresponds to the duration of the release of usable vapour therefrom. This pre-determined period is counted by the PCB, which then shuts down the heater 3 once it has elapsed.

After use the user can remove the removable container 6 from the device 1 so it can be replaced with another. They remove the mouthpiece 15 from the opening 13 and manually remove the removable container 6 from the heating chamber 4. This can be done by inverting the device 1 so the removable container 6 falls out, or the mounting flange 38 can be manually lifted from the mounting platform 21. The spent removable container 6 can then be disposed of, and another loaded into the device 1 in its place.

The remaining figures show eight further designs of removable container which are all used in a similar way to removable container 6 described above, but which all comprise alternative design features. In each case they provide support for the second aspect of the present invention, which relates to removable containers as such.

Figure 4:
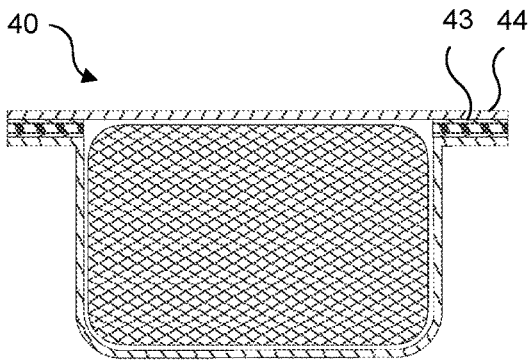
FIG. 4 is a cross-sectional side view of a second removable container according to the second aspect of the present invention.
Figure 5:
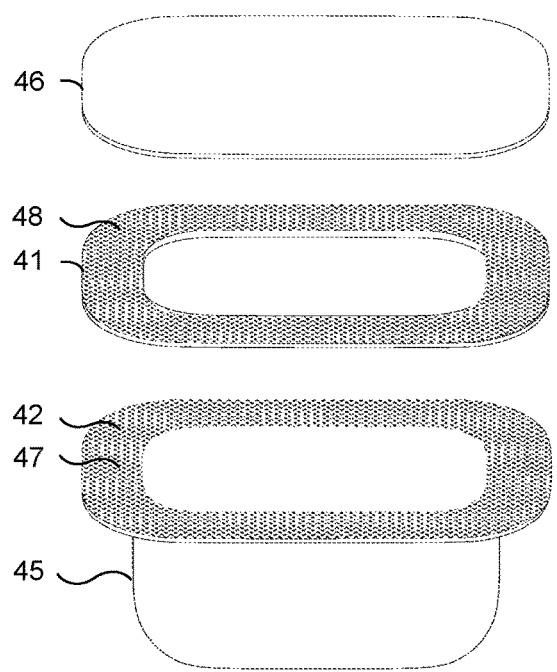
FIG. 5 is an exploded perspective view of the second removable container as shown in FIG. 4.

FIGS. 4 and 5 show a second removable container 40 which is similar to removable container 6 described above, except that a strengthening member 41 is arranged between the first connection region 42 and the second connection region 43. The strengthening member 41 is made from a plastics material and it serves to maintain the mounting flange 44 in a rigid laterally extending shape.

Further, the body portion 45 and the lid portion 46 are made from a non heat sealable filter paper material which contains polyester fibres. A first ultrasonic weld component 47 is then used to bond the strengthening member 41 to the first connection region 42, and a second ultrasonic weld component 48 is used to bond the strengthening member 41 to the second connection region 43. Known ultrasonic weld application techniques are used to create these bonds.

With the mounting flange 44 being more rigid it is easier to manually manipulate in use. The strengthening member 41, as well as the ultrasonic weld components 47 and 48 are able to withstand the temperatures they are subjected to in use, which are the same as those described above.

It will be appreciated that with this construction no heat sealable filter paper material is located inside the heating chamber 4. This means that no plastic fibres contained inside such material are heated during use, which happens with removable container 6 described above. As such, with removable container 40 no undesirable by-products of heating heat sealable filter paper are produced, and no such material melts such that it can form an undesired bond with any adjacent part.

Figure 6:
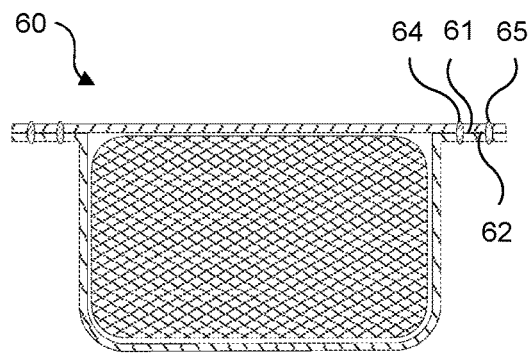
FIG. 6 is a cross-sectional side view of a third removable container according to the second aspect of the present invention.
Figure 7:
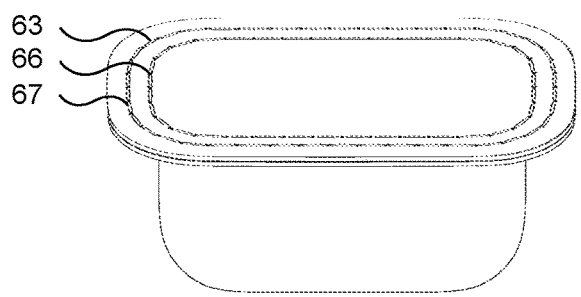
FIG. 7 is a perspective view of the third removable container as shown in FIG. 6.

FIGS. 6 and 7 show a third removable container 60 which is the same as removable container 6 described above, except that instead of a heat seal component, the first connection region 61 and the second connection region 62 are connected by a stitching component 63. Two pieces of thread 64 and 65 are used to create two lines of stitching 66 and 67. The thread 64 and 65 is able to withstand the temperatures it is subjected to in use, which are the same as those described above. With this construction it is not necessary to use filter paper material with any plastics fibres for heat sealing or ultrasonic welding purposes for the removable container 60, so a simpler filter paper material without such elements is used instead.

It will be appreciated that the method of manufacture of removable container 60 will involve the use of a sewing function, which may be preferred for ease of manufacture or to save costs.

Figure 8:
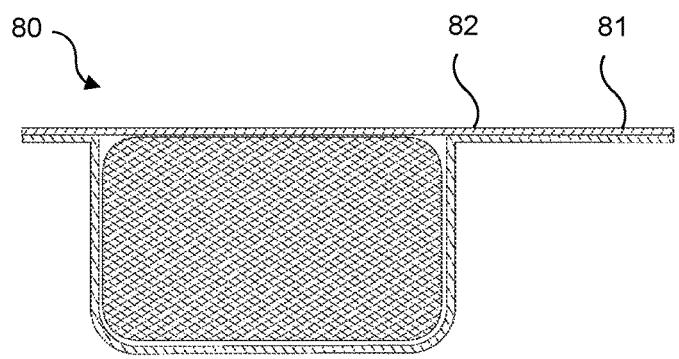
FIG. 8 is a cross-sectional side view of a fourth removable container according to the second aspect of the present invention.
Figure 9:
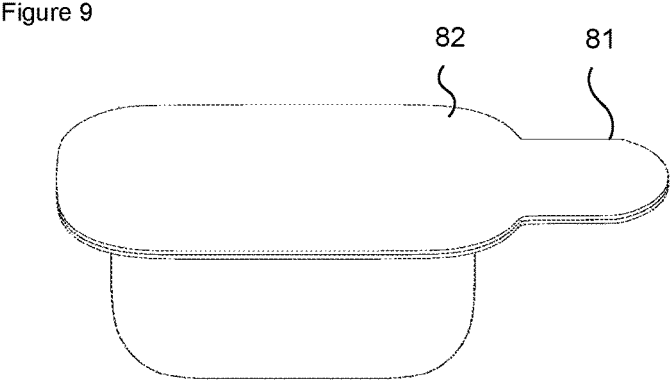
FIG. 9 is a perspective view of the fourth removable container as shown in FIG. 8.

FIGS. 8 and 9 show a fourth removable container 80 which is the same as removable container 6 described above, except that it comprises a laterally extending handle portion 81. The handle portion 81 extends to one side from the mounting flange 82, and provides a convenient place for the user to hold the removable container 80 in use.

A vapour producing device with which the removable container 80 is used (not shown) would comprise a seating area in which the handle portion 81 is located when the removable container is disposed in the heating chamber, which seating area would laterally extend from a mounting platform like that described above.

Figure 10:
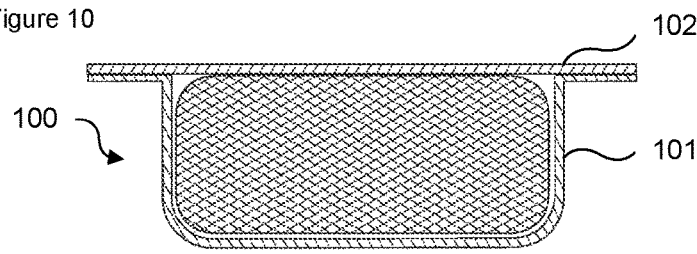
FIG. 10 is cross-sectional side view of a fifth removable container according to the second aspect of the present invention.
Figure 11:
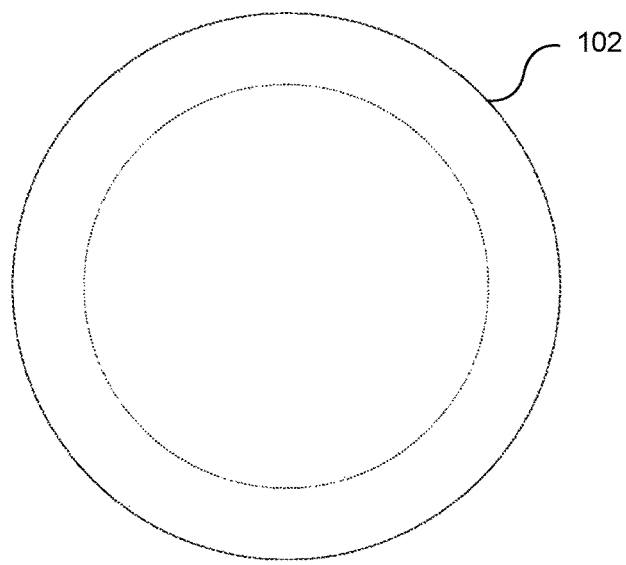
FIG. 11 is a top view of the fifth removable container as shown in FIG. 10.

FIGS. 10 and 11 show a fifth removable container 100 which is the same as removable container 6 described above except that the body portion 101 and the lid portion 102 are annular instead of being rectangular.

A vapour producing device with which the removable container 100 is used (not shown) would comprise an annular heating chamber adapted to receive the removable container 100. Such vapour producing devices are known, and they comprise an annular heating chamber on their side, which is closed with a cover.

There are known manufacturing methods which could be adopted to readily produce removable container 100, which may be preferred for ease of manufacture or to save costs.

Figure 12:
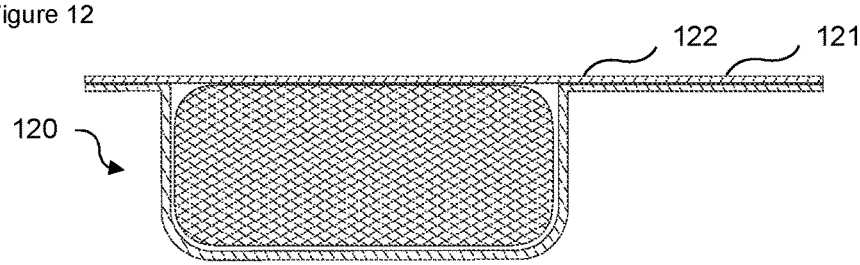
FIG. 12 is cross-sectional side view of a sixth removable container according to the second aspect of the present invention.
Figure 13:
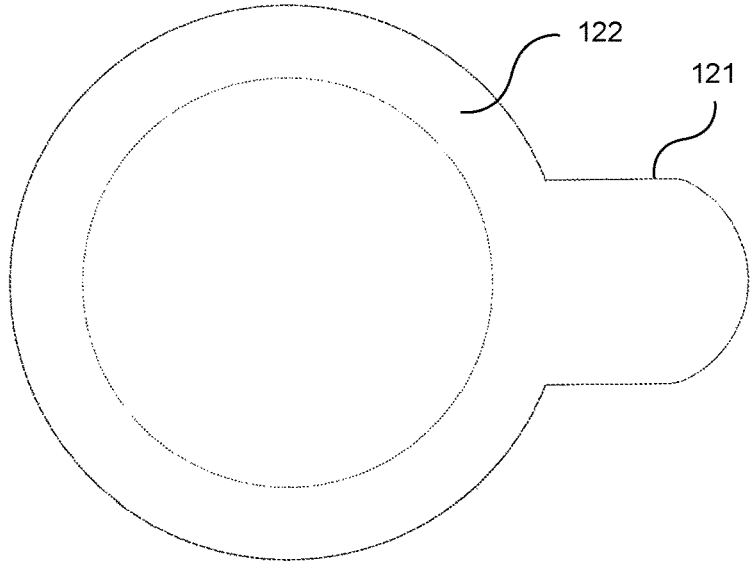
FIG. 13 is a top view of the sixth removable container as shown in FIG. 12.

FIGS. 12 and 13 show a sixth removable container 120 which is the same as removable container 100 described above, except that it comprises a laterally extending handle portion 121. The handle portion 121 extends to one side from the mounting flange 122, and provides a convenient place for the user to hold the removable container 120 in use.

A vapour producing device with which the removable container 120 is used (not shown) would comprise a seating area in which the handle portion 121 is located when the removable container 120 is disposed in the heating chamber, which seating area would laterally extend from a mounting platform like that described above, although it would be annular and not rectangular.

Figure 14:
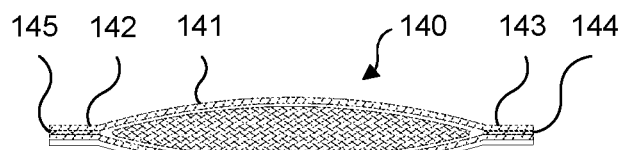
FIG. 14 is cross-sectional side view of a seventh removable container according to the second aspect of the present invention.
Figure 15:
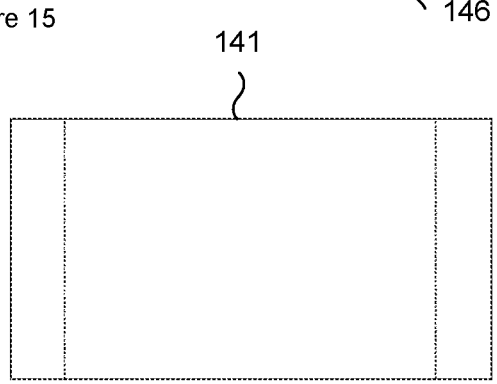
FIG. 15 is a top view of the seventh removable container as shown in FIG. 14.
Figure 16:
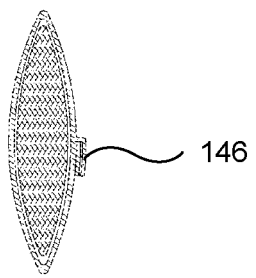
FIG. 16 is a cross-sectional end view of the seventh removable container as shown in FIG. 14.

FIGS. 14 to 16 show a seventh removable container 140 which is formed from a tube of material 141 which is closed at both ends 142 and 143 by adhesive components 144 and 145. In other respects the removable container 140 works like those described above, it just has a more simplex shape. It is suitable for placement in a heating chamber which has a similar shape to it. The removable container 140 is more like a tea bag in construction, which may be preferred for manufacturing or ease of use requirements. As adhesive components 144 and 145 are used here, the removable container 140 is made from a simple filter paper material without any plastics fibres for heat seal or ultrasonic welding purposes.

The tube of material 141 is formed from a single piece of material which is formed into a tube and secured in that configuration with a crimped axially extending seam 146.

Figure 17:
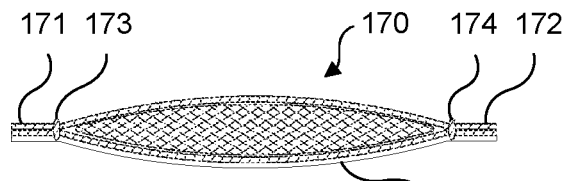
FIG. 17 is cross-sectional side view of an eighth removable container according to the second aspect of the present invention.
Figure 18:
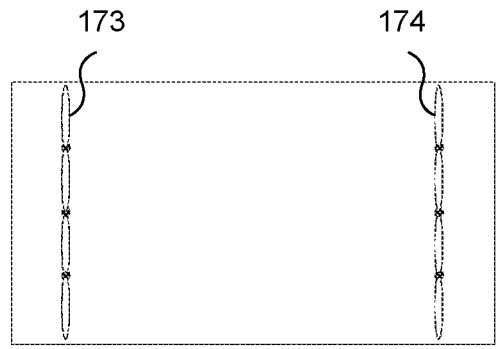
FIG. 18 is a top view of the eighth removable container as shown in FIG. 17.
Figure 19:
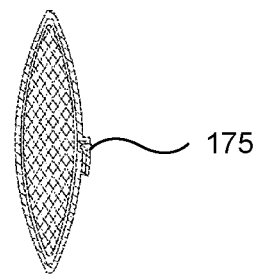
FIG. 19 is a cross-sectional end view of the eighth removable container as shown in FIG. 17.

FIGS. 17 to 19 show an eighth removable container 170 which is the same as removable container 140 described above, except that instead of adhesive components to close both ends 171 and 172, lines of stitching 173 and 174 are used. Further, the material is secured in a tube configuration with another line of stitching 175. Again, this approach may be preferred for manufacturing reasons.

Figure 20:
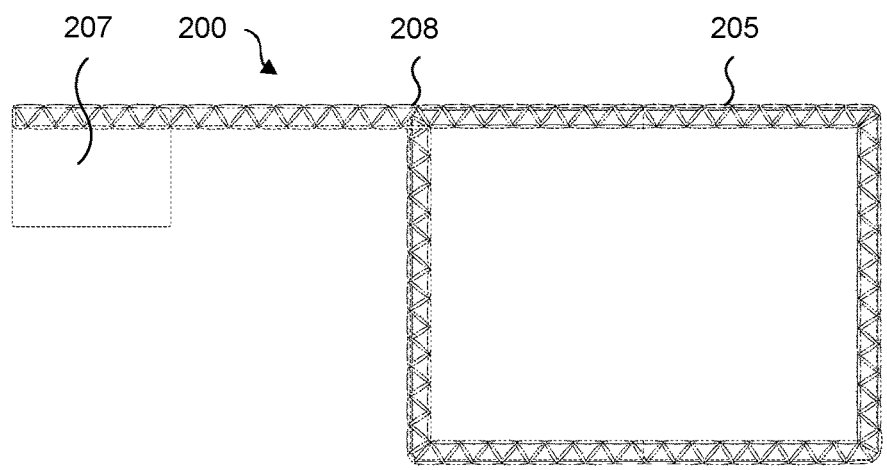
FIG. 20 is top view of a ninth removable container according to the second aspect of the present invention.
Figure 21:
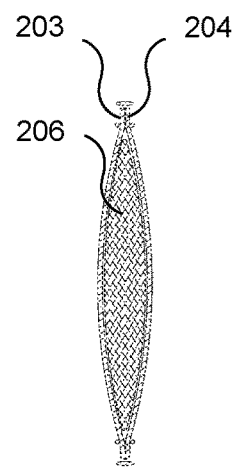
FIG. 21 is a cross-sectional end view of the ninth removable container as shown in FIG. 20.
Figure 22:
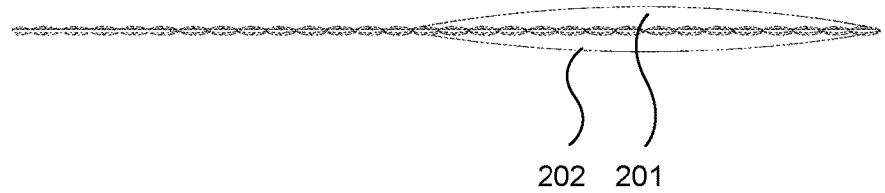
FIG. 22 is a side view of the ninth removable container as shown in FIG. 20.

Finally, FIGS. 20 to 21 show a ninth removable container 200 which comprises a rectangular first part 201 connected to a corresponding rectangular second part 201. In this embodiment the first part 201 and the second part 202 are made from a woven muslin material. A peripheral region 203 of the first part 201 is connected to a peripheral region 204 of the second part 202 by connection means in the form of a stitching component 205. During manufacture the first part 201 and the second part 202 can be connected around three of their corresponding sides to form a container comprising an opening. The herbal vapour producing material 206 can then be placed in the container through the opening, before the opening is then stitched closed. (Alternatively, if the manufacturing process allows for it, the first part 201 and the second part 202 of the removable container 200 can be wrapped around the herbal material 206 before they are then connected together in a single stitching function.)

Removable container 200 also comprises a substantially L-shaped mounting handle 207 which extends laterally from one corner 208 of the removable container 200. The handle 207 is secured in place with the stitching component 205. This construction provides a ready way to manually manipulate the removable container 200 in use, and to locate it in a vapour producing device with which it is used (not shown). In particular the mounting handle 207 can be disposed in a seating area of a corresponding shape, to help secure the removable container 200 in place.

The second aspect of the present invention defines a removable container for use in creating a vapour producing device as claimed in any of claims 1 to 15 below, in which the removable container comprises a vapour permeable membrane enclosing a herbal vapour producing material to be heated. The various embodiments shown in FIGS. 2 to 22 provide full support for the second aspect of the present invention.

A vapour producing device can be altered from that described above without departing from the scope of claim 1. In particular, in an alternative embodiment (not shown) the heating chamber is arranged on the side of the device, and a cover is used to close it. In another alternative embodiment (not shown), the heating chamber is annular instead of rectangular in shape.

A removable container can be altered from those described above without departing from the scope of claim 16. In particular, in alternative embodiments (not shown) the vapour permeable membranes are made from paper materials, plastics materials, alternative plastics reinforced paper materials, alternative woven materials or perforated metal materials.

In other alternative embodiments (not shown) removable containers are manufactured from continuous tubes of material produced via extrusion or helical winding techniques. Such tubes are cut to size, filled with herbal material and then closed at both ends.

In another alternative embodiment (not shown) the vapour permeable membrane perishes when the removable container is heated by the heater in use.

In another alternative embodiment (not shown) a removable container is like removable container 40 described above, except that instead of a strengthening member made from a plastics material, a strengthening member made from a card material is used instead. It has a heat sealable plastics material coated onto each side, which is used to form bonds with the body portion and the lid portion, as an alternative to ultrasonic welds. This construction is more sustainable than using a plastics strengthening member. As with removable container 6, the heat seals which connect the body portion and the lid portion sit outside the heating chamber 4 in use because the mounting flange rests on the mounting platform 21, and as such they will not be heated to the same temperature as the body portion. This means that the bonds between the first connection region and the strengthening member and between the second connection region and the strengthening member should not fail in use. In another alternative embodiment (not shown), another removable container is the same as that described above except that an adhesive is used to connect the card strengthening member to the body portion and the lid portion, instead of a heat sealable plastics material.

Finally, in other alternative embodiments (not shown) features from one of the above embodiments are combined with features from another of the above embodiments. For example, in one a strengthening member is present, as well as a lateral handle.

Therefore, the first and second aspects of the present invention overcome the problems associated with known herbal vaporisers, by providing a convenient removable container for the herbal material to be consumed. The removable container can be produced as a consumable product, which can be placed in the vapour producing device for consumption in a simplex action, and then removed therefrom after the herbal product has been heated, again in a simplex action. This removes the requirement to load the device manually with loose herbal material, and to empty it of loose spent material.

Furthermore, the use of a removable container ensures that the correct quantity of herbal material is used each time, and that is it heated in a more regular and efficient fashion. A user can also more easily track and regulate their consumption.

The invention claimed is:

1. A vapour producing device comprising a power supply, a heater powered by said power supply, a heating chamber heated by said heater and a vapour outlet, in which a removable container is disposed in said heating chamber, said removable container comprising a vapour permeable membrane enclosing a herbal vapour producing material to be heated,
in which said heating chamber comprises a receptacle area with an inner surface of a pre-determined three-dimensional shape, in which said removable container is formed with a shape which substantially corresponds with said pre-determined three-dimensional shape,
in which said removable container comprises a laterally extending handle portion, and in which said device comprises a seating area in which said handle portion is located.

2. A vapour producing device comprising a power supply, a heater powered by said power supply, a heating chamber heated by said heater and a vapour outlet, in which a removable container is disposed in said heating chamber, said removable container comprising a vapour permeable membrane enclosing a herbal vapour producing material to be heated,
in which said removable container comprises a body portion, an opening formed in said body portion, and a lid portion closing said opening, in which said body portion comprises a first connection region, in which said lid portion comprises a second connection region, in which said first connection region and said second connection region are connected together by a connection means comprising one or more of a heat seal component, an adhesive component, an ultrasonic weld, a crimping component, a stitching component, a staple component or a punched material component, in which said body portion comprises a rim which defines said opening, in which said first connection region comprises a flange extending substantially parallel with said opening, in which said lid portion is planar and in which said second connection region comprises a peripherally extending region of said lid portion.

3. A vapour producing device comprising a power supply, a heater powered by said power supply, a heating chamber heated by said heater and a vapour outlet, in which a removable container is disposed in said heating chamber, said removable container comprising a vapour permeable membrane enclosing a herbal vapour producing material to be heated,
in which said removable container comprises a first part partially connected to a second part so as to form a container comprising an opening, in which said removable container comprises a connection means closing said opening comprising one or more of a heat seal component, an adhesive component, an ultrasonic weld, a crimping component, a stitching component, a staple component or a punched material component.

4. A vapour producing device comprising a power supply, a heater powered by said power supply, a heating chamber heated by said heater and a vapour outlet, in which a removable container is disposed in said heating chamber, said removable container comprising a vapour permeable membrane enclosing a herbal vapour producing material to be heated,
in which said removable container is formed from a tube of material which is closed at both ends by one or more of a heat seal component, an adhesive component, an ultrasonic weld, a crimping component, a stitching component, a staple component or a punched material component.

5. A removable container for use in creating a vapour producing device comprising a power supply, a heater powered by said power supply, a heating chamber heated by said heater and a vapour outlet, in which a removable container is disposed in said heating chamber, said removable container comprising a vapour permeable membrane enclosing a herbal vapour producing material to be heated,
in which said removable container comprises a body portion, an opening formed in said body portion, and a lid portion closing said opening, in which said body portion comprises a first connection region, in which said lid portion comprises a second connection region, in which said first connection region and said second connection region are connected together by a connection means comprising one or more of a heat seal component, an adhesive component, an ultrasonic weld, a crimping component, a stitching component, a staple component or a punched material component, in which said body portion comprises a rim which defines said opening, in which said first connection region comprises a first flange extending substantially parallel with said opening, in which said lid portion is planar and in which said second connection region comprises a peripherally extending region of said lid portion.

6. A removable container for use in creating a vapour producing device comprising a power supply, a heater powered by said power supply, a heating chamber heated by said heater and a vapour outlet, in which a removable container is disposed in said heating chamber, said removable container comprising a vapour permeable membrane enclosing a herbal vapour producing material to be heated,
in which said removable container is formed from a tube of material which is closed at both ends by one or more of a heat seal component, an adhesive component, an ultrasonic weld, a crimping component, a staple component or a punched material component.

* * * * *